(12) United States Patent
Leung (10) Patent No.: US 10,272,255 B2
(45) Date of Patent: Apr. 30, 2019

(54) METHOD OF FORMING A NEGATIVE ION EMITTING PRODUCT AND A PRODUCT FORMED BY SUCH METHOD

(75) Inventor: Wing Chan Leung, Fotan (HK)

(73) Assignee: YBS Graphene Company Limited, Seoul (KR)

( * ) Notice: Subject to any disclaimer, the term of this patent is extended or adjusted under 35 U.S.C. 154(b) by 271 days.

(21) Appl. No.: 14/343,623

(22) PCT Filed: Sep. 7, 2012

(86) PCT No.: PCT/CN2012/081155
§ 371 (c)(1),
(2), (4) Date: Aug. 22, 2014

(87) PCT Pub. No.: WO2013/034104
PCT Pub. Date: Mar. 14, 2013

(65) Prior Publication Data
US 2014/0378741 A1    Dec. 25, 2014

(30) Foreign Application Priority Data

Sep. 8, 2011 (HK) .................. 11109467.2

(51) Int. Cl.
*A61N 2/06* (2006.01)
*A61N 1/10* (2006.01)

(52) U.S. Cl.
CPC .............. *A61N 2/06* (2013.01); *A61N 1/10* (2013.01); *Y10T 29/49591* (2015.01)

(58) Field of Classification Search
CPC ........ A61N 1/10; A61N 2/06; Y10T 29/49591
(Continued)

(56) References Cited

U.S. PATENT DOCUMENTS 5,067,255 A * 11/1991 Hutcheson ........... A43B 17/026
                                                                 36/28
5,696,240 A * 12/1997 Vallarino ................ C07F 5/003
                                                                 424/9.361
(Continued)

FOREIGN PATENT DOCUMENTS

CN    1654739    8/2005
CN    2925153    7/2007

OTHER PUBLICATIONS

English Translation of CN1654739A (attached as CN1654739A_English_Translation.pdf), Jul. 25, 2007, whole document.*
(Continued)

*Primary Examiner* — Navin Natnithithadha
*Assistant Examiner* — Sunita Reddy
(74) *Attorney, Agent, or Firm* — Renner Kenner Greive Bobak Taylor (57) ABSTRACT

Provided is a negative ion emitting product and a method of forming the same. The negative ion emitting product comprises a silicone substrate and a separate silicone insert or patch material containing a negative ion emitting source. The separate silicone insert or patch material is attached to a surface of said substrate or inserted into a space defined by a wall of said substrate. The product is designed to be worn by a human or animal and preferably comprises a bracelet, necklace, collar, watch strap, shoe insole or the like. It particularly comprises a double molded silicone product containing in the patch or insert material, but not the substrate, nano-particles of negative ion radiating rare earth powder.

13 Claims, 5 Drawing Sheets

(58) Field of Classification Search
USPC ................ 600/15; 29/896.411; 128/897–899
See application file for complete search history.

(56) References Cited

U.S. PATENT DOCUMENTS

| | | | | |
|---|---|---|---|---|
| 6,615,491 B1* | 9/2003 | Kaizuka | ............... | A44C 5/0023 29/896.4 |
| 2003/0098420 A1* | 5/2003 | Fujino | ....................... | A61L 9/01 250/423 R |
| 2004/0042965 A1* | 3/2004 | Usui | ....................... | A61F 7/034 424/40 |
| 2004/0149732 A1* | 8/2004 | Usui | ....................... | A61F 7/034 219/528 |
| 2006/0088602 A1* | 4/2006 | Cioca | ....................... | A61K 8/19 424/634 |
| 2007/0020317 A1* | 1/2007 | Yeung | ....................... | C08K 3/34 424/443 |
| 2007/0066739 A1* | 3/2007 | Odle | ....................... | C08J 7/047 524/430 |
| 2007/0079424 A1* | 4/2007 | Cho | ....................... | A42C 5/02 2/195.1 |
| 2007/0095254 A1 | 5/2007 | Momose | | |
| 2007/0292463 A1* | 12/2007 | Spector | ................ | A61K 8/0208 424/401 |
| 2008/0041099 A1* | 2/2008 | Hirata | ................ | A44C 5/0023 63/15 |
| 2008/0156672 A1* | 7/2008 | Shih | .......................... | A23L 3/26 206/217 |
| 2011/0106227 A1* | 5/2011 | Desiderio | ................. | A61F 7/02 607/111 |
| 2012/0121883 A1* | 5/2012 | Tee | .......................... | B32B 13/02 428/292.1 |
| 2012/0220814 A1* | 8/2012 | Young | ................... | A61M 21/00 600/15 |
| 2012/0226095 A1* | 9/2012 | Young | ................... | A61M 21/00 600/15 |
| 2012/0289773 A1* | 11/2012 | Joshi | ...................... | A61B 17/29 600/104 |
| 2012/0317843 A1* | 12/2012 | Bove | ................... | A43B 1/0054 36/25 R |
| 2013/0192514 A1* | 8/2013 | Murdough | .............. | G09F 11/00 116/222 |
| 2013/0211296 A1* | 8/2013 | Chau | ........................ | A43B 1/00 601/17 |
| 2014/0234210 A1* | 8/2014 | Lin | .......................... | A61K 9/14 424/1.21 |

OTHER PUBLICATIONS

English Translation of CN2925153Y (attached as CN2925153Y_English_Translation.pdf), Aug. 17, 2005, whole document.*

* cited by examiner

METHOD OF FORMING A NEGATIVE ION EMITTING PRODUCT AND A PRODUCT FORMED BY SUCH METHOD

FIELD OF THE INVENTION

The invention relates to a method of forming a negative ion emitting product and a product formed by said method. The invention relates particularly, but not exclusively, to a method for forming a wellness bracelet, collar or similar such device to be worn by a human or animal.

BACKGROUND OF THE INVENTION

As health issues are receiving more and more attention today, an increasing number of products that generate, emit or radiate negative ions are being released into the market. According to studies conducted by some research institutions around the world negative ions are believed to strengthen the body's immune system, enhance metabolism, alleviate stress and depression and help the body recovery from fatigue.

About 60 to 70% of the human body is composed of bodily fluid containing electrolytes and non-electrolytes. Electrolytes are composed of balanced negative and positive ions and it is widely believed that if this balance is compromised the human body will become more vulnerable to various illnesses. It is recognized within the medical profession that any difference in the distribution of ions enclosing human cells is significantly related to the body's nerve cells, and this may have an influence on the recovery of health or deterioration of an illness.

Negative and positive ions exist by using cellular walls as barriers, the cellular wall permeability differing in accordance with the amount of positive, negative, and dipolar electric potentials. Ions may move around the human body influenced by the strength or distribution of energy in the internal and external environment.

Electromagnetic fields (EMFs) are all around us, being generated by every day devices such as laptop computers, coffeemakers, televisions, and cellular phones as well as coming from broadcast sources and the like. Studies on what EMFs do to human and animal bodies suggest some disturbing results. In a recent study, it was suggested that mobile phone use may cause brain tumors through extended use of the mobile phone close to a user's head. Negative ions are believed to help counteract EMFs, which is just one of the benefits of using a negative ion emitting product on one's person.

Examples of recent negative ion generating household products include air conditioners, air humidifiers, air purifiers and vacuum cleaners which incorporate a piezo-electric negative ion generator. As it is commonly believed by the medical profession that around 80% of negative ions are absorbed through the skin whereas only 20% are inhaled, negative ion emitting personal accessory products worn in direct contact with the skin, such as bracelets and necklaces, are becoming increasingly popular with the general public.

One type of negative ion emitting or radiating personal wellness accessory product comprises a one-piece moulded silicone based bracelet containing in the silicone material a negative ion generating source material in powder form. However, it was found that mixing such powder in the silicone raw material prior to moulding had two significant disadvantages. Firstly, the powder weakened the molecular structure of the moulded silicone strap causing it to tear relatively easily by contrast with a strap moulded from pure silicone, i.e. from silicone not containing the powder. Secondly, the inclusion of the powder also changed the intended colour of the resulting product from that of the original colour of the silicone raw material. This was especially obvious in the case of white silicone where the resulting bracelet strap after moulding had a dull grey colour rather than the pristine white of the raw silicone material. Consequently, it was necessary to apply a pure white spray coating to the strap after moulding to regain the intended white colour in the final product. It has, however, been found that the spray coating is not durable for continuous use being partially depleted within a period of one to two months of normal use leading to erasure of the coating on parts of the bracelet strap and thus giving a worn look to the bracelet. Consequently, there is a need to address these and other problems associated with such negative ion emitting personal wellness accessory products.

OBJECTS OF THE INVENTION

An object of the invention is to mitigate or obviate to some degree one or more problems associated with negative ion emitting products and particularly, but not exclusively, to such products as negative ion emitting personal wellness accessory products.

The above object is met by the combination of features of the main claim; the sub-claims disclose further advantageous embodiments of the invention.

One skilled in the art will derive from the following description other objects of the invention. Therefore, the foregoing statement of object is not exhaustive and serves merely to illustrate some of the many objects of the present invention.

SUMMARY OF THE INVENTION

In a preferred arrangement, the invention provides a negative ion emitting product and a method of forming the same. The negative ion emitting product comprises a silicone substrate and a separate silicone insert or patch material component containing a negative ion emitting source. The separate silicone insert or patch material is attached to a surface of said substrate or inserted into a space defined by a wall of said substrate. The product is designed to be worn by a human or animal and preferably comprises a bracelet, necklace, collar, watch strap, insole for a shoe or the like. It particularly comprises a double moulded silicone product containing in the patch or insert material, but not the substrate, nano-particles of negative ion radiating rare earth powder.

In a first main aspect of the invention, there is provided a method of forming a negative ion emitting product comprising the steps of: forming a substrate; and attaching to a surface of said substrate or inserting into a space defined by said substrate a material containing a negative ion or anion emitting source.

Preferably, the substrate is formed of a polymer material which is moldable, but other substrate materials may be used such as leather or cloth or any material from which an article for wearing by an animal or human may be made. The polymer material may be formed of a polymer material such as silicone including silicon, carbon, hydrogen and oxygen.

Preferably, the negative ion or anion emitting source is formed of a rare earth material and, more preferably, formed of nano-sized particles of said rare earth material which may comprise a powder formed from a mixture of different rare earth materials such as any of Scandium ($Sc_{21}$), Yttrium ($Y_{39}$) and/or any one or more of the fifteen lanthanide series of elements.

The material containing a negative ion emitting source is a separate component of the product to the substrate. The material containing a negative ion emitting source may also be formed from a polymer material using silicone as a base material and may have the negative ion emitting source injected or mixed therein.

An advantage of forming the material containing a negative ion emitting source as a separate component to the substrate is that, in contrast to conventional products in which the rare earth powder material is mixed or inserted into the material of the substrate, the rare earth material in the present invention does not discolour or compromise the structural integrity of the silicone substrate. Furthermore, it negates the need to spray paint the substrate to recover its original or an intended colour.

In one embodiment, the negative ion emitting product is formed by an extrusion process such that a wall of the substrate defines a space and wherein the material containing a negative ion emitting source is inserted into said space defined by the extruded substrate as a step of the extrusion process.

In an alternative embodiment, the material containing a negative ion emitting source is inserted into said space by a double moulding process whereby the substrate is double moulded around the material containing a negative ion emitting source.

In yet another embodiment, the material containing a negative ion emitting source is formed as a sheet form component such that said sheet form component can be attached to a surface of the substrate by any suitable means including a double moulding process. In the case of a double moulding process, the substrate may be formed by moulding as a first moulding step and the sheet form component double moulded to a surface of the substrate. However, although not preferred, a reverse double moulding process may be performed whereby the sheet form component is created by the first moulding step and the substrate is double moulded to a surface of the sheet form component.

Preferably, the substrate is formed with at least one generally planar recess in which the sheet form component of material containing a negative ion emitting source locates when it is attached to a surface of the substrate.

The negative ion emitting product is preferably adapted to be worn by a human or an animal for well-being reasons and may comprise a bracelet, necklace, a watch strap, a collar, an insole for a shoe or the like. The product may be adapted to be worn such that the material containing a negative ion emitting source is placed next to a human or animal's skin.

Alternatively, the negative ion emitting product may comprise a part of an electronic device such as a shell or housing for the electronic device. This is particularly useful for a portable handheld electronic devices such as mobile phones which are suspected of emitting harmful electromagnetic radiation.

In a second main aspect of the invention, there is provided a negative ion emitting product comprising: a substrate; and a material containing a negative ion emitting source attached to a surface of said substrate or inserted into a space defined by said substrate.

The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figures, of which.

DESCRIPTION OF PREFERRED EMBODIMENTS

The following description is of preferred embodiments by way of example only and without limitation to the combination of features necessary for carrying the invention into effect.

The invention can be better understood with reference to the following figures. The components in the figures are not necessarily to scale with emphasis instead being placed upon illustrating the features of the various embodiments of the invention.

Moreover, in the figures, like reference numerals designate corresponding parts throughout the different views.

An objective of one of the preferred embodiments of the product of the invention is to fill a market niche for high quality wellness bracelets that provide the wearer with a much higher therapeutic level of negative ion radiation than the negative ion silicone bracelets currently in the market place.

In some example embodiments, this is achieved by using nano-particles of a rare earth powder mixture (any of Scandium, Yttrium and/or any of the Lanthanide series of elements) mixed into a component of the product. In some embodiments, the rare earth powder mixture may operate as an negative ion emitting source. The rare earth powder mixture may be supplemented by including in the product Germanium 32, and/or rare earth Neodymium magnets, which may, in some embodiments, be arranged to generate negative ions. In some example applications, these embodiments are advantageous in that the absorption of the negative ion radiation through the skin is boosted by the magnetic energy field created by the magnets, but the inclusion of the magnets is not essential to the present invention.

In a first attempt to provide a suitable product, the applicant designed a one piece moulded silicone strap (not shown) containing within the silicone base material nano-particles of negative ion radiating rare earth powder. Neodymium magnets encased in stainless steel bullet containers, were inserted and held securely in place in the strap.

The individual magnetic bullet components were constructed of a magnetized cylindrically-shaped Neodymium component inserted into an open-ended cylindrical stainless steel tube which was then sealed with a force-fitted stainless steel cap. Each of the individual magnetic bullets was then inserted into individually moulded cylindrical sections of the moulded one piece silicone strap. The cylindrical magnetic bullets were held securely in place within the one piece silicone strap by larger diameter size end caps.

An amount of 8% by weight of the rare-earth powder was added to the silicone raw material prior to moulding of the silicone strap and this generated in the moulded strap a negative ion emission rate of 1,800 to 2,000 ions/cc as measured by a Eco-Holistic EB-13 hand-held ion tester.

It was found, however, that this initial design exhibited the aforedescribed problems with the strength of the resulting strap being compromised by the presence of the powder in the silicone material and the colour of the resulting strap being not as desired and requiring spray painting to regain a desired final product finish. Consequently, this design was not proceeded with as it did not adequately address the aforementioned problems despite providing an enhanced negative ion emission rate over conventional devices.

Figure 1:
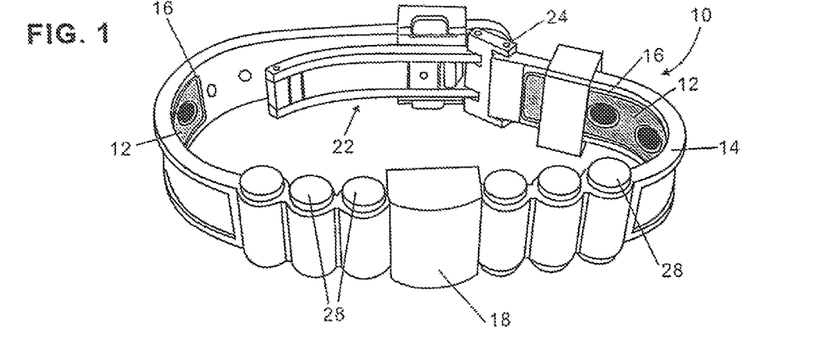
FIG. 1 is a perspective view from the front of a negative ion emitting personal wellness accessory product according to a first embodiment of the invention.
Figure 2:
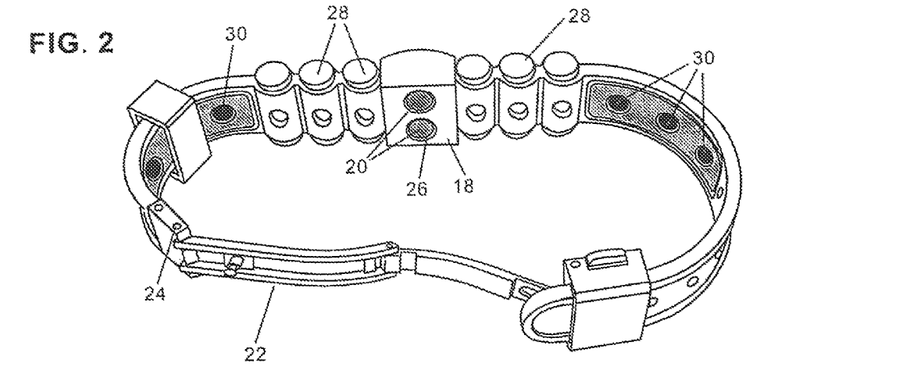
FIG. 2 is a perspective view from the rear of the accessory product of FIG. 1 with a clasp mechanism in an open position.
Figure 3:
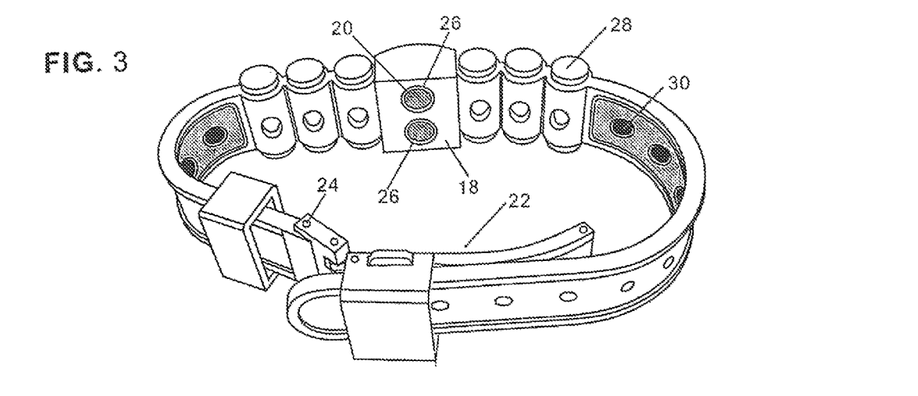
FIG. 3 is a perspective view from the rear of the accessory product of FIG. 1 with a clasp mechanism in a closed position.

To overcome the above problems, the applicant has redesigned the silicone bracelet 10 so as to include in one preferred embodiment as illustrated by FIGS. 1 to 3 one or more individual negative ion silicone insert components 12 positioned on the underside (rear side) of the strap 10 by means of a double-moulding manufacturing process. The main body or substrate 14 of the silicone strap 10 is manufactured using a pure silicone base material, thereby both maintaining the integrity of the strap strength and also eliminating the need to use spray coating to aesthetically achieve the pure colour required for outer appearance of the moulded strap 10. By adding in the order of 15% by weight of negative ion emitting powder to each individual silicone insert component 12, this achieves the same enhanced level of negative ion emission rate as achieved with the discontinued design, i.e. an overall negative ion emission rate of 1,800 to 2,000 ions/cc for the whole bracelet 10.

The negative ion emitting product of FIGS. 1 to 3 comprises a bracelet 10 designed to be worn by a human, but it may be formed as a necklace, collar, watch strap or the like.

The bracelet 10 is formed by a double moulding process such that the product contains in the patch material 12, but not the substrate 14, nano-particles of negative ion radiating rare earth powder comprising a powder formed from a mixture of different rare earth materials such as any of Scandium ($Sc_{21}$), Yttrium ($Y_{39}$) and/or any one or more of the fifteen Lanthanide series of elements.

The patch material 12 is a separate component of the product to the substrate 14 and may also be formed from a polymer material using silicone as a base material and may have the negative ion emitting source material injected or mixed therein. The patch material 12 is formed as a sheet form insert that locates into a correspondingly shaped generally planar recess 16 in a rear surface of the strap 10. As such, in use, the patch material 12 containing the rare earth powder is located next to a wearer's skin.

An advantage of forming the patch component 12 as a separate component to the strap substrate 14 is that, in contrast to products in which the rare earth powder material is mixed or inserted into the material of the substrate, the rare earth material in the present invention does not discolour or compromise the structural integrity of the silicone substrate 14. Furthermore, it negates the need to spray paint the substrate 14 to recover its original or an intended colour.

Whilst a double moulding process is preferred, the patch material 12 can be attached or affixed to a surface of the strap 10 by any suitable means. In the case of a double moulding process, the strap substrate 14 may be formed by moulding as a first moulding step and the patch component 12 then double moulded onto a surface of the substrate 14. However, although not preferred, a reverse double moulding process may be performed whereby the patch component 12 is created by the first moulding step and the strap substrate 14 is then double moulded to a surface of the sheet form component or components 12, where there are more than one.

More specifically, the product of FIGS. 1 to 3 comprises the moulded silicone strap 10 incorporating two silicone patch inserts 12 each containing the nano-size particles of negative ion generating rare-earth powder, rare-earth Neodymium magnetic components, a central design accent component 18 affixed with pure Germanium 32 components 20 and a two-button spring clasp mechanism 22 to provide a one size fits all bracelet 10. The silicone strap 10 is connected to the stainless steel two-button spring clasp mechanism 22 by a stainless steel spring mechanism link pin 24. However, it will be understood that any suitable clasp or other fastening mechanism to fasten the strap may be utilized.

The stainless steel central design accent component 18 is fitted with two pure Germanium 32 components 20 affixed to the base of the central accent. The pure Germanium 32 components 20 are each securely held in place by a force-fitted stainless steel collar 26. The central design accent component 18 has an open slot (not shown) to allow it to slide over the silicone strap 10 to be held securely in the centre of the bracelet 10.

The negative ion radiation function of the two moulded silicone patch components 12 affixed to the inner surface of the one-piece moulded silicone strap 10 is achieved by adding in the order of 15% by weight of the nano-sized particle mixture of Scandium, Yttrium and/or the Lanthanide series elements to a pure silicone raw material prior to the double injection-moulding manufacturing process. However, it will be understood that the % by weight of the rare earth powder mixture may be increased if only one patch insert 12 is employed and may be decreased if more than two such patch inserts 12 are used. It is intended that the % amount by weight of rare earth powder mixture added to the patch insert material is selected to provide a resultant negative ion radiation rate for the bracelet in the range of about 1,800 to 2,000 ions/cc.

The stainless steel bullet components 28 are kept so as to mimic the discontinued bracelet design, but without the rare-earth Neodymium magnet component inserts. Force-fit caps of said bullets are securely glued to overcome a problem of the caps falling-off. To provide the magnetic field to boost the absorption of negative ions through the skin, rare-earth Neodymium components 30 may be embedded immediately below the surface of the double-moulded silicone inserts 12. Thus, the method of forming the bracelet may include the step of placing Neodymium magnetic components 30 in the recesses 16 on the back of the strap 10 prior to double moulding the rare earth patch components 12 into said recesses 16. Alternatively, the Neodymium magnetic components 30 may be attached or inserted into the patch components 12 prior to the second moulding process to attach the patch components 12 to the strap substrate 14.

Consequently, the shape and positioning of the rare-earth Neodymium magnet components 30 are changed from the initial design of the bracelet such that the Neodymium components 30 are changed from cylindrically-shaped Neodymium components contained within the stainless steel bullets 28 to round tablet-shaped Neodymium components 30 as seen in the drawings.

Figure 4:
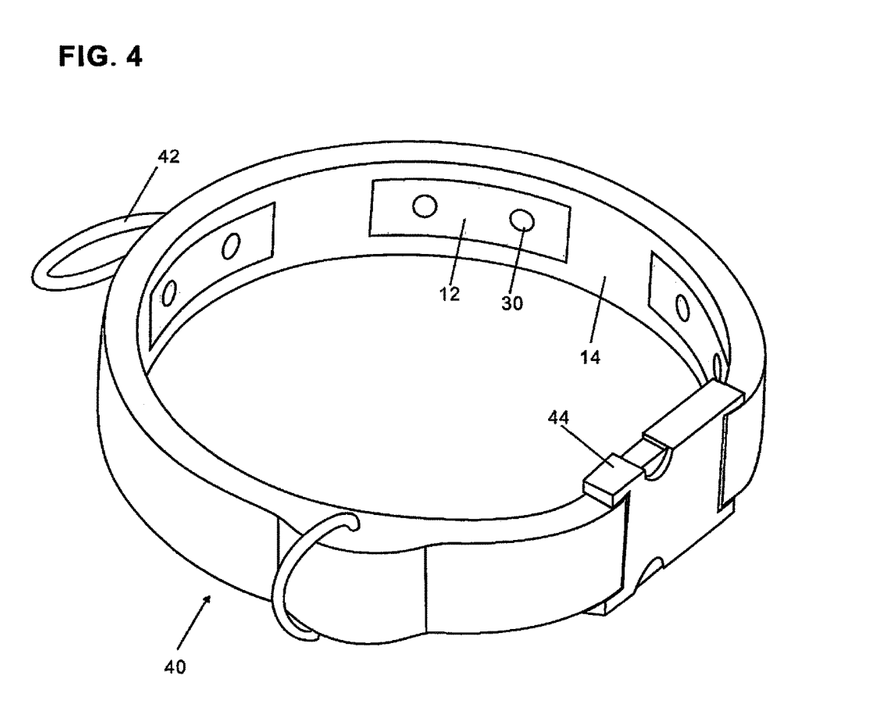
FIG. 4 is a perspective view from the front of a negative ion emitting personal wellness accessory product according to a second embodiment of the invention.

FIG. 4 shows another preferred embodiment of the invention comprising a pet collar 40. This has a structure largely similar to that of the bracelet 10 of FIGS. 1 to 3 save for the (possible) inclusion of means 42 for securing a lead (not shown) to the collar 40 and an alternative fastening means 44 to a clasp mechanism for fastening the collar 40 around the neck of a pet.

Figure 5:
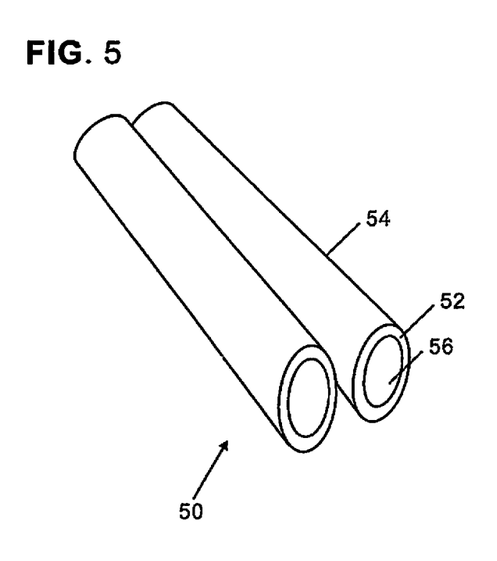
FIG. 5 is a perspective view of a negative ion emitting product according to a third embodiment of the invention.

FIG. 5 shows a further embodiment of the invention which comprises negative ion emitting product 50 having a substrate 52 which defines a space therein. In this embodiment, the substrate 52 comprises at least one extruded tube 54 surrounding an insert material 56 containing a negative ion emitting source. In this embodiment, the negative ion emitting product 50 is formed by an extrusion process wherein the material 56 containing a negative ion emitting source is inserted into the space defined by a wall of the extruded substrate 52 as a further step of the extrusion process to the forming of the extruded tube 54. A negative ion emitting product 50 of the type disclosed by this embodiment can be utilized to make necklaces or other articles to be worn by a person or an animal.

Figure 6:
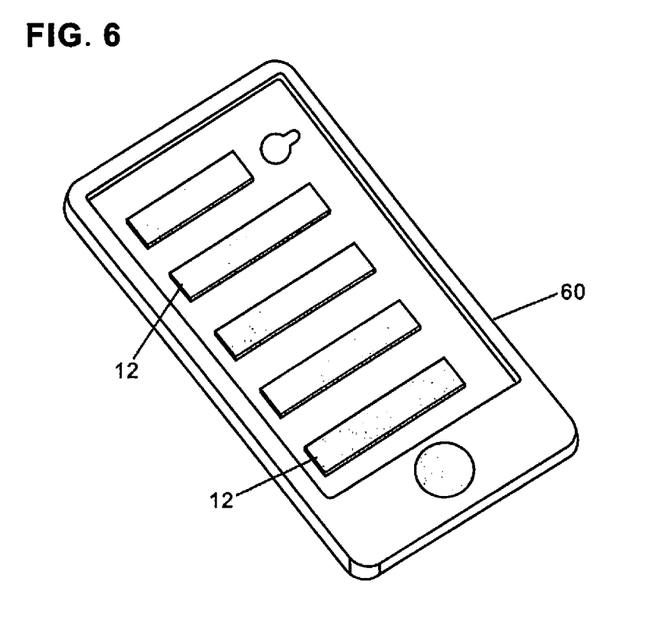
FIG. 6 is a perspective view of a part of a housing or shall for an electronic device according to a fourth embodiment of the invention.

FIG. 6 shows yet another embodiment of the invention comprising a part of an electronic device (not shown) such as a shell or housing 60 for the electronic device. More particularly, this embodiment comprises a shell or housing part 60 of a portable handheld electronic device such as a mobile phone for counteracting the harmful effects on a user of electromagnetic radiation emitted by the portable electronic device.

In this embodiment, one or more patch components 12 containing the rare earth powder mixture as hereinbefore described are attached, preferably by a double moulding process to an inside surface of the device housing or shell 60. However, in some arrangements, the patch components 12 are attached to an outside surface of the device housing or shell.

Figure 7:
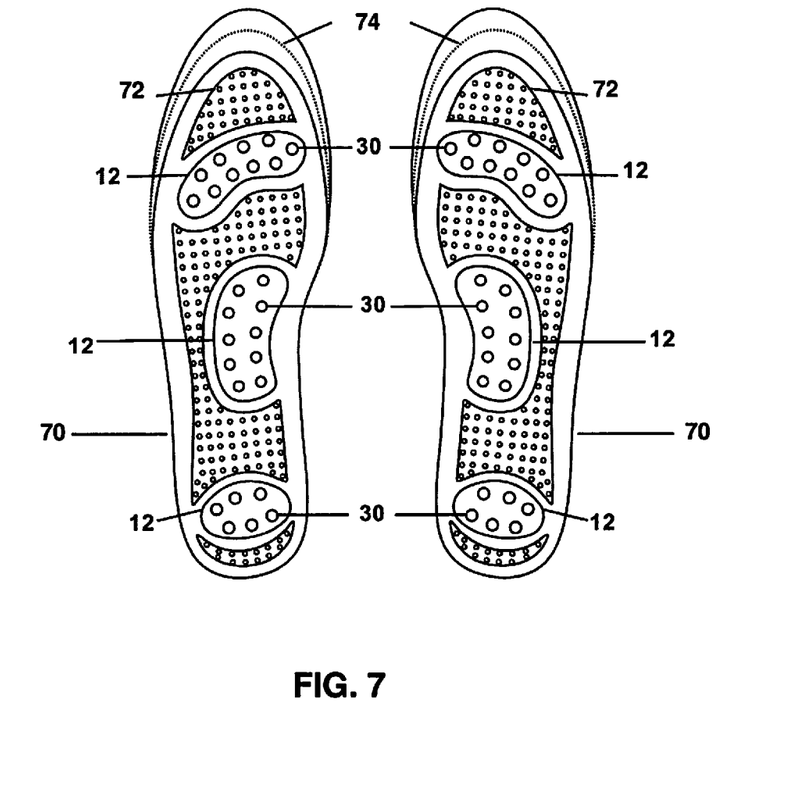
FIG. 7 is a top plane view of a pair of insoles for shoes according to a fifth embodiment of the invention.

FIG. 7 shows a further embodiment of the invention comprising a pair of insoles 70 for a pair of shoes arranged to support a person's feet. In this embodiment, the insole comprises Neodymium magnetic components 30 or other negative ion generating member embedded inside one or more patch components 12. In one embodiment, these patch components 12, together with the Neodymium magnetic components or other negative ion generating member, may also be double-moulded to a silicone substrate to form the insole. Preferably, the insole 70 is also provided with a plurality of holes 72 for ventilation and thus offers additional comfort for a user.

In another embodiment, each of the insole 70 may be provided a dieline 74 along which the insole can be cut and fitted into shoe of smaller size.

In general, the invention provides a negative ion emitting product and a method of forming the same. The negative ion emitting product comprises a silicone substrate and a separate silicone insert or patch material containing a negative ion emitting source. The separate silicone insert or patch material is attached to a surface of said substrate or inserted into a space defined by a wall of said substrate. The product is designed to be worn by a human or animal and preferably comprises a bracelet, necklace, collar, watch strap or the like. It particularly comprises a double moulded silicone product containing in the patch or insert material, but not the substrate, nano-particles of negative ion radiating rare earth powder.

While the invention has been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art.

The invention claimed is:

1. A method of forming a negative ion emitting product comprising the steps of:
   molding a substrate comprising silicone;
   attaching a rare-earth magnetic component to the substrate; and
   attaching a separate material to a surface of said substrate by a double molding process or inserting, by a double molding process, the separate material into a space defined by said substrate, wherein the separate material comprises a negative ion emitting source and a silicone material; and wherein Germanium is arranged on the substrate in addition to the separate material; and wherein the negative ion emitting source comprises a rare-earth material powder mixture comprising Scandium, Yttrium and any one or more of the Lanthanide series of elements.

2. The method of claim 1, wherein the substrate is formed of silicone.

3. The method of claim 1, wherein the rare earth magnetic component is a Neodymium magnetic component.

4. The method of claim 1, wherein the rare-earth material powder mixture is a nano-particle rare-earth material powder mixture.

5. The method of claim 1, wherein a wall of the substrate defines a space and wherein the separate material is inserted into said space, whereby the substrate is double molded around the separate material.

6. The method of claim 1, wherein the separate material is formed as a sheet form component.

7. The method of claim 1, wherein the negative ion emitting product is formed as a bracelet, necklace, collar or insole for a shoe configured to be worn by a human or an animal.

8. The method of claim 1, wherein the negative ion emitting product comprises a shell or housing for an electronic device.

9. A negative ion emitting product comprising:
- a molded substrate comprising silicone;
- a rare-earth magnetic component attached to the molded substrate; and
  - a separate material comprising a negative ion emitting source and a silicone material, wherein the separate material is double molded and is attached to a surface of said molded substrate or inserted into a space defined by said molded substrate; and wherein Germanium is arranged on the substrate in addition to the separate material; and
  - wherein the negative ion emitting source comprises a rare-earth material powder mixture comprising Scandium, Yttrium and any one or more of the Lanthanide series of elements.

10. The negative ion emitting product of claim 9, wherein the substrate is formed of silicone.

11. The negative ion emitting product of claim 9, wherein the magnetic component is a Neodymium magnetic component.

12. The negative ion emitting product of claim 9, wherein the rare-earth material powder mixture is a nano-particle rare-earth material powder mixture.

13. The negative ion emitting product of claim 9, wherein the negative ion emitting product is a bracelet, necklace, collar or insole for a shoe configured to be worn by a human or an animal.

\* \* \* \* \*